(12) United States Patent
Manasek

(10) Patent No.: US 7,195,619 B2
(45) Date of Patent: Mar. 27, 2007

(54) ABSORBENT ARTICLE FOR PROTECTION AGAINST ANAL LEAKAGE

(76) Inventor: Francis J. Manasek, P.O. Box 706, Norwich, VT (US) 05055

(*) Notice: Subject to any disclaimer, the term of this patent is extended or adjusted under 35 U.S.C. 154(b) by 0 days.

(21) Appl. No.: 10/750,344

(22) Filed: Dec. 31, 2003

(65) Prior Publication Data

US 2004/0162537 A1    Aug. 19, 2004

Related U.S. Application Data

(60) Provisional application No. 60/437,522, filed on Dec. 13, 2002.

(51) Int. Cl.
*A61F 13/15* (2006.01)

(52) U.S. Cl. ............ 604/385.01; 604/378; 604/385.01; 604/385.17

(58) Field of Classification Search ........... 604/385.01, 604/359, 378, 380, 358, 385.17, 385.18
See application file for complete search history.

(56) References Cited

U.S. PATENT DOCUMENTS

| | | | | |
|---|---|---|---|---|
| 24,385 A | * | 6/1859 | Flanders | ............... 125/29 |
| 4,681,577 A | | 7/1987 | Stern et al. | |
| 4,880,417 A | * | 11/1989 | Yabrov et al. | ............... 604/355 |
| 5,593,398 A | * | 1/1997 | Weimer | ............... 604/359 |
| 5,665,081 A | * | 9/1997 | Grosse | ............... 604/359 |
| 5,713,886 A | | 2/1998 | Sturino | |
| 6,313,371 B1 | * | 11/2001 | Conant et al. | ............... 604/359 |
| 6,350,258 B1 | | 2/2002 | Markoweicki | |
| 6,436,080 B1 | | 8/2002 | Carlucci et al. | |
| 6,913,573 B1 | * | 7/2005 | Viscomi et al. | ............... 600/29 |
| 2002/0087132 A1 | | 7/2002 | Samuelsson | |

* cited by examiner

*Primary Examiner*—Jacqueline F. Stephens
(74) *Attorney, Agent, or Firm*—Norma E. Henderson

(57) ABSTRACT

An anal region pantyliner, has an impervious outer layer, an absorbent middle layer, and a liquid-permeable bodymost layer. It is preferably held in place against an undergarment by removable adhesive. It absorbs anal leakage and fits both male and female anatomy. A unique feature of one embodiment is a pear-like shape having a wide area covering the buttocks and a narrow part extending forward between the legs, terminating short of the genital area comfortable for both males and females. An alternate female version continues forward to cover the vaginal or urethral region. The preferred embodiment is thicker in the crotch area, having an absorbent pad situated retro-scrotally along the center and an additional inter-buttock absorbent ridge. An alternate embodiment has an absorbent dam situated retro-scrotally. Another alternate embodiment is flat, being of uniform thickness.

17 Claims, 9 Drawing Sheets

ABSORBENT ARTICLE FOR PROTECTION AGAINST ANAL LEAKAGE

RELATED APPLICATIONS

This application claims priority to U.S. Provisional Application Ser. No. 60/437,522, filed Dec. 31, 2002.

FIELD OF THE INVENTION

The invention relates to personal sanitary products and, in particular, to an absorbent article worn to absorb anal leakage.

BACKGROUND

Anal leakage is a recognized medical problem and is widespread. A significant percentage of the adult population, both male and female, suffers from anal incontinence of one form or another. It has been described as "one of the most psychologically and socially debilitating conditions in an otherwise healthy individual" (Seymour, Stephen D., "Fecal Incontinence", emedicine, Dec. 3, 2002).

Anal incontinence, also called fecal incontinence, is the loss of anal sphincter control leading to unwanted or untimely release of feces. It can range from total incontinence to very minor, where the patient may pass only small amounts of flatus or mucous. Minor anal incontinence generally causes embarrassing soiling. In addition to incontinence, such soiling can also result from hemorrhoids, fistulae, or the application of topical medicaments. There is a wide spread in reported incidence, but it is generally agreed that over 2% of the general adult population suffers from some degree of anal incontinence. The condition is actually probably underreported: only 30% of people with anal incontinence have spoken about it with their physician and only about 5% had it noted on their medical charts. It is not a topic that is generally discussed and is consequently often considered shameful.

It has been estimated that $400 million is spent on adult diapers each year. In the United States, if the generally reported 2% incidence is accepted, there are 6 million anal incontinents. This figure is probably far lower than actual, and does not include the hemorrhoid population, which is about 5% of the general population, or about 15 million.

It is further estimated that between 15 and 35% of patients with anal fistulae have post-operative incontinence, depending to some extent upon the procedure used. The incidence is 8.6 cases per 100,000 population: in men, the incidence is 12.3 cases per 100,000 population, and in women, the incidence is 5.6 cases per 100,000 population. Of women with multiple births, about 26% have some form of post partum anal incontinence and 30% of women over the age of 65 have anal incontinence to some degree, often associated with urinary incontinence. The incidence in males increases in the over-50 age group. Incontinence increases with advancing age, and as our population ages the need for protection will increase. Incontinence products are currently the fastest-growing items of the personal absorbent market.

Current practical solutions to the problem exist in the form of absorbent undergarments such as diaper-like devices, or waterproof pants with absorbent liners. These are generally designed primarily for urinary incontinence and, because of anatomical considerations, are most successful in females. They are generally bulky, uncomfortable, and difficult for the wearer to conceal.

Many individuals suffer from anal leakage of less severe form than total fecal incontinence. This problem generally ranges from mild leakage of mucous to occasional, intermittent leaks of small amounts of feces. Additionally, there are some disorders, such as hemorrhoids, where it is particularly difficult to clean the affected area after defecation, a situation that creates the possibility of soiling one's undergarments. There are some items designed to deal with fecal incontinence or uncontrollable diarrhea. Some of these have cup-shaped reservoirs, or are diaper-like underpants.

Minor anal incontinence, such as loss of mucous or minor fecal leakage, does not warrant the bulk and inconvenience of the incontinence undergarments currently on the market. Thinner absorbents, such as pantyliners, can potentially provide protection against staining and may be readily worn without being visible. However, current pantyliners and other external absorbent catamenial products are designed for the female anatomy, being specifically designed to cover the vaginal area. As such, they are not particularly well suited to covering the anal region. Successful coverage of this area requires special design.

As mentioned, there are adult "diaper"-like absorbents, and for the lighter cases, there are women's pantyliners. None are satisfactory for minor incontinence. All diaper-like products are bulky, relatively expensive, and uncomfortable. The pantyliner and absorbent pad, designed for catamenial purposes, bunches up in the crotch area and fails to cover the anal region adequately, often resulting in leakage, staining, and discomfort. Most absorbent articles meant to be worn beneath undergarments are intended for use to control menstrual discharge, vaginal exudates in women or urethral incontinence in either sex. Absorbent articles designed for men are generally those dealing with urinary incontinence such as post-surgical incontinence. Disposable panties also exist, some with pantyliner-like padding in the genital and anal areas, but these are typically not secure over the anal region, as well as being rather indiscreet with respect to the wearer's problem.

Physical exercise, such as athletic activity or physical labor, can also result in profuse sweating that will also leak through, and stain undergarments and outerwear. The volume of such leakage can be readily accommodated by the absorbent materials currently employed in the vaginal-oriented pantyliners designed specifically for females. However, the pantyliners currently available are designed to absorb menstrual flow or vaginal secretions. As such, they are products that speak to female discharge and therefore address specifically the female anatomy. These designs are generally in the "hour-glass" shape (for example, U.S. Pat. No. 6,436,080) or rectangular, with or without rounded edges (for example, U.S. Pat. Pub. No. 2002/0087132A1). A few designs are more complex, and are designed for wear by women with thongs or "G" strings (for example, U.S. Pat. No. 6,350,258 and U.S. Pat. No. 5,713,886). While many of these items have a tapered shape, they are specifically constructed for covering, and absorbing leakage from, the vaginal area, while generally leaving the anal region completely exposed, thus making them obviously unsuitable for use in absorbing discharge from the anal region.

The design of current pantyliners therefore does not make them comfortable to wear, nor particularly suited to either sex, for the control of anal discharge. Although they may function well when used on the female anatomy to control vaginal discharge or urethral incontinence, they are of inappropriate shape, thickness, and size to effectively contain anal leakage in either the male or female. In particular, the typical hourglass shaped pantyliner, when worn to contain anal exudates, has one wide end of the device crimped into the crotch, where it chafes, particularly (in the male) the posterior scrotum. It is uncomfortable and, since it does not conform to the body, may permit leakage. The narrow middle portion is not wide enough to guarantee bridging the inter-buttock cleft and the other wide portion of the hourglass liner is not wide enough to cover the anal region with confidence. Further, normal lateral shifting of the undergarment may displace it enough to permit leakage.

A prior art anal incontinence product is disclosed in U.S. Pat. No. 4,681,577 (Stem et al). It appears that the purpose of the product of Stem et al is to contain large volumes of feces and urine in a device for the totally incontinent female. The device of Stem et al is essentially a semirigid boat-shaped container, from 0.25 to 2 inches deep, filled with absorbent material in a particular manner. The front portion of the Stem et al device is specifically designed to collect urine and will not work for males where the external genitalia will get in the way and prevent close body contact.

In short, no current product deals successfully with light anal leakage or offers suitable, comfortable protection from anal soiling, whatever the etiology. Devices designed to accommodate severe fecal incontinence are too bulky and uncomfortable to wear when only a lesser problem exists. What has been needed, therefore, is an absorbent pantyliner that is specifically designed to absorb minor leakage or other soiling from the anal area, that stays secure during sports and other activities, and that is comfortable and secure for males as well as females.

SUMMARY

These and other objectives are met by the present invention, which is an anatomically-designed absorbent article for protection against anal soiling in adults. The present invention provides a unique form of absorbent sanitary device, specifically adapted for the absorption of anal exudates.

The present invention is an anal region pantyliner, with an impervious outer layer, an absorbent middle layer, and a porous inner layer. It is preferably held in place against the undergarment by removable adhesive. It is specifically designed to absorb anal leakage and is of a unique design to fit the male anatomy as well as the female.

Conventional materials and machines are used to easily and inexpensively manufacture the present invention. A unique feature of this product is its shape, which is pear-like in outline, with the wide area covering the buttocks and the narrow part extending forward between the legs. It terminates short of the genital area, so it is as comfortable for males as for females. If desired, an alternative female version can be constructed that continues forward to cover the vaginal or urethral region.

While there are many possible embodiments of the present invention, they fall into three general categories. The preferred embodiment is thicker in the crotch area with an absorbent ridge along the center, having an additional inter-buttock absorbent ridge. An alternative embodiment is thicker in the crotch area to absorb more exudate, having an absorbent dam situated retro-scrotally. Another alternative embodiment is flat, being of uniform thickness. All embodiments are anatomically suited for the male anatomy.

DETAILED DESCRIPTION

The present invention is an anal region pantyliner, with an impervious outer layer, an absorbent middle layer, and a porous inner layer. It is preferably held in place against the undergarment by removable adhesive applied to the back of the outer layer. It is specifically designed to absorb anal leakage and is of a unique design to fit the male anatomy as well as the female. The present invention specifically covers the anal region and is intended to be worn inside panties or jockey shorts to provide protection in cases of light anal soiling. It is effective, discrete, and comfortable for both males and females.

Conventional materials and machines are used to easily and inexpensively manufacture the present invention. A unique feature of this product is its shape, which is pear-like in outline, with the wide area covering the buttocks and the narrow part extending forward between the legs. It terminates short of the genital area (scrotum or vagina), so it is as comfortable for males as for females. If desired, an alternative female version can be constructed that continues forward to cover the vaginal or urethral region. The present invention therefore provides protection from soiling from mild anal discharge, hemorrhoids, applied medicaments, or any situation that makes cleaning the anal area difficult. It is a uniquely shaped panty liner with no semi-rigid or rigid containment components. It is not generally intended to catch urine.

While there are many possible embodiments of the present invention, they fall into three general categories. The preferred embodiment (FIGS. 1–3) is thicker in the crotch area, having an absorbent pad situated retro-scrotally along the center and an additional inter-buttock absorbent ridge. An alternative embodiment (FIGS. 4–6) is thicker in the crotch area to absorb more exudates, having an absorbent dam situated retro-scrotally. Another alternative embodiment (FIGS. 7 and 8) is flat, being of uniform thickness. All embodiments are anatomically suited for the male anatomy.

The present invention is of particular use to the general population of males and females with mild anal incontinence, post-partum women, individuals with hemorrhoids, post-operative hemorrhoidectomy patients, patients with anal fistulae or other conditions that require the topical application of medicaments, or other post-operative patients. It can also be used as a general cleanliness device, much as female pantyliners are used as items to be worn daily. A particular advantage of the present invention is that it can be easily and successfully used by males, obviating the embarrassment and discomfort of buying and wearing ill-fitting female pads.

Figure 1:
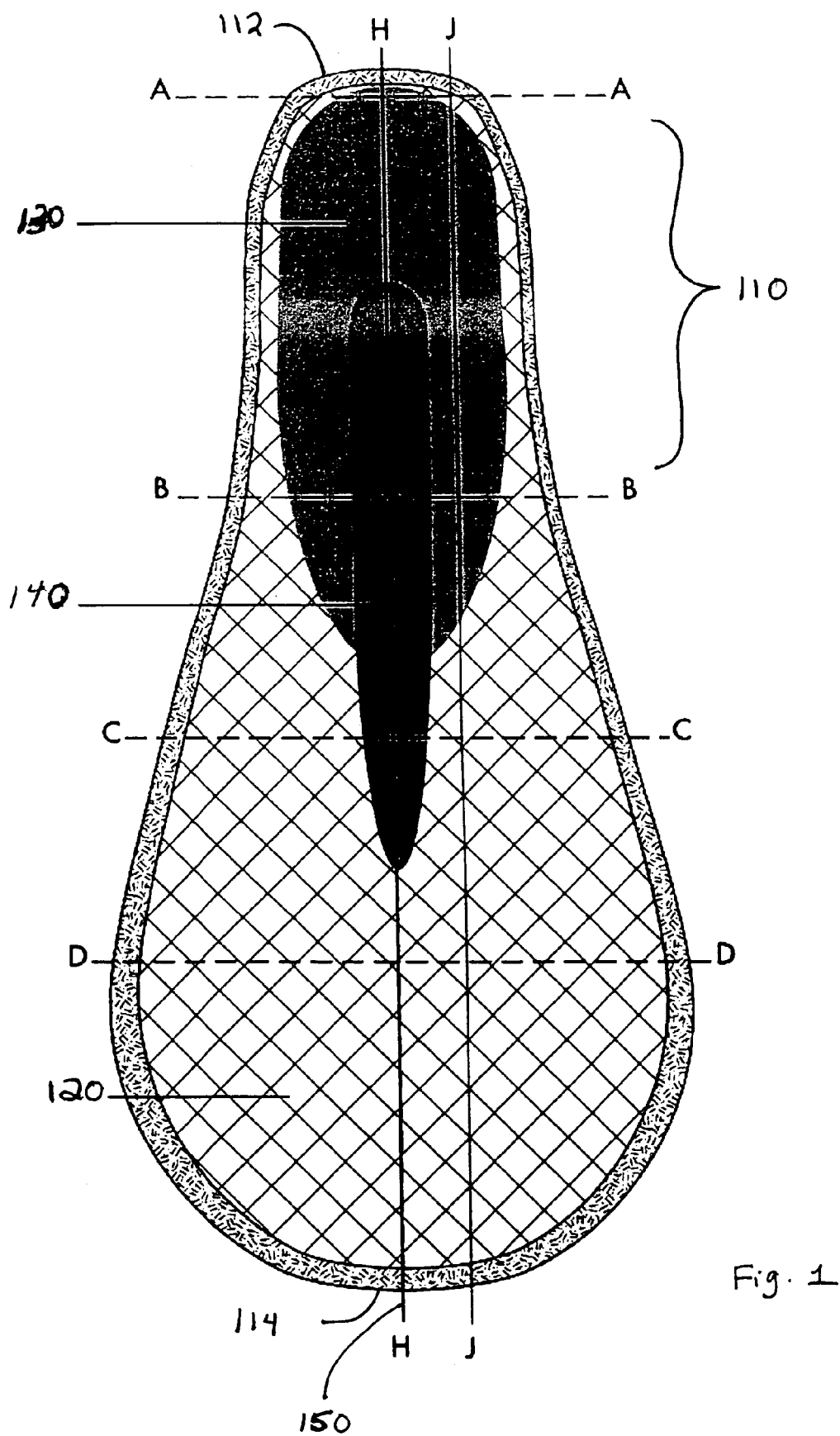
FIG. 1 is a top view of a preferred embodiment of the present invention.

Although the male undergarment is not usually referred to as a "panty", this invention is being described as a "pantyliner" because the term is a sufficiently well-known descriptor. The pantyliner of the present invention has a unique design anatomically constructed to fit the male anatomy. A top view of a preferred embodiment of the present invention is depicted in FIG. 1. Gourd, or pear-shaped, it is narrow at the end 110 (portion A-B) that lies in the crotch and abuts the posterior edge of the scrotum in the male. The length of portion A-B 110 is such that narrow end 112 abuts the scrotum when properly applied, but does not ride over it, eliminating scrotal irritation. The liner widens laterally as it emerges posteriorly from the crotch and continues to widen as it extends dorsad over the buttocks to wide end 114, covering the anal area and a sufficient surrounding area on each buttock to prevent leakage. This area is made sufficiently wide so that normal lateral displacement of underwear, even during athletic activities, does not displace the absorbent item enough to result in leakage. The main portion 120 of the pad, extending over the buttock region, is typically of substantially uniform thickness throughout.

Frequently, however, anal leakage, in an individual who is either sitting or standing, runs downward into the buttock cleft. This embodiment of the present invention addresses this problem specifically by providing pad 130 of additional absorbent material that substantially thickens the pantyliner in the narrow region. Although material of greater absorbency can be used in this region, it is also important to have sufficient bulk to act as a physical dam and ensure contact with the skin. The narrowness of this region substantially eliminates discomfort and maximizes the contact with the body. Thickened area 130 is shaped so that it narrows as it emerges from the crotch to minimize visibility, yet lies within the most ventral portion of the buttock cleft, where fluid drains and where the need for absorbency is the greatest.

To deal with more copious leakage, the basic design is further modified in this preferred embodiment by adding narrow longitudinal midline ridge 140 that fits into the buttock cleft. With longitudinal ridge 140, lateral displacement of the entire liner is minimized and absorbency at the point of leakage is increased. The length, width, and thickness of ridge 140 can be varied along midline 150 depending upon size of the device and the amount of anal exudate it is designed to control.

Figure 2:
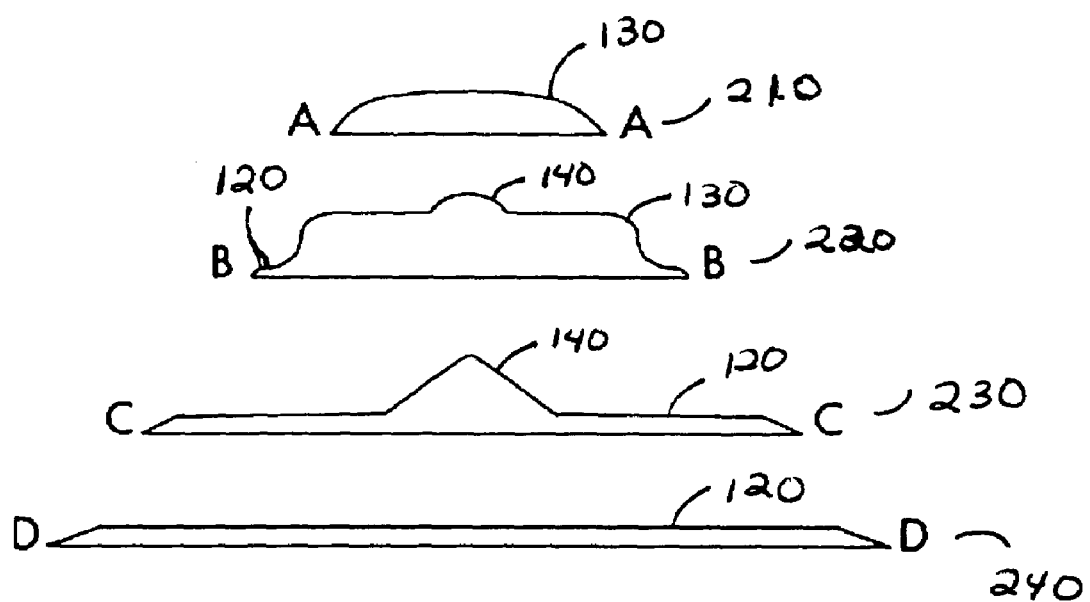
FIG. 2 depicts four transverse sectional views of the embodiment of FIG. 1.

The unique thickness variations in this embodiment of the present invention are depicted in FIG. 2. Transverse sections 210, 220, 230, 240 correspond to lettered cross-sectional lines in FIG. 1. In FIG. 2, section A—A 210 has pad 130 providing a dam of moderate thickness in the lower buttock region. Section B—B 220 has outer edges comprised of main pad 120, a middle area comprised of moderately thick pad 130, and central ridge 140. Section C—C 230 is largely comprised of main pad 120, but also has the outer extension of ridge 140. Section D—D 240 is comprised entirely of main pad 120.

Figure 3:
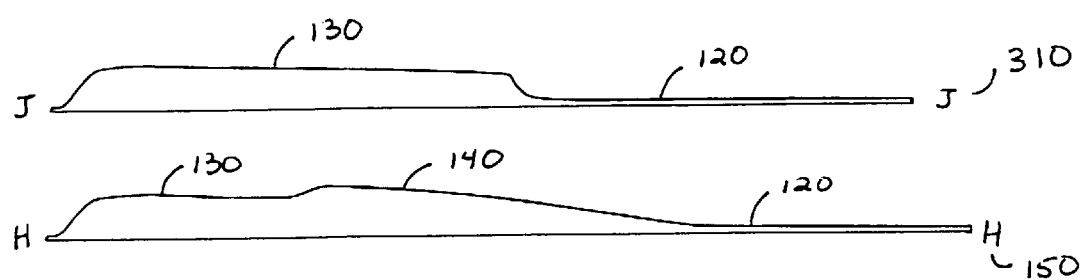
FIG. 3 depicts two longitudinal sectional views of the embodiment of FIG. 1.

FIG. 3 depicts longitudinal sections 310, 320 corresponding to lines H—H and J—J of FIG. 1. In FIG. 3, section J—J 310 is comprised partially of main pad 120 and moderately thick pad 130. Section H—H along midline 150 is comprised of three sections: main pad 120, moderately thick pad 130, and ridge 140.

The liner of the present invention is preferably manufactured using conventional female pantyliner technologies. The outermost layer is impervious to liquid; there is a middle absorbent layer, and the top, or bodymost layer, is liquid-permeable. The layers are sealed in a conventional way around the periphery of the device to prevent leakage. Conventional female pantyliner adhesive technology can be used to affix this invention to close-fitting male or female underpants. The wider parts 120 are typically about as thick as a regular female pantyliner but region 130 and ridge 140 are thicker as described.

Figure 4:
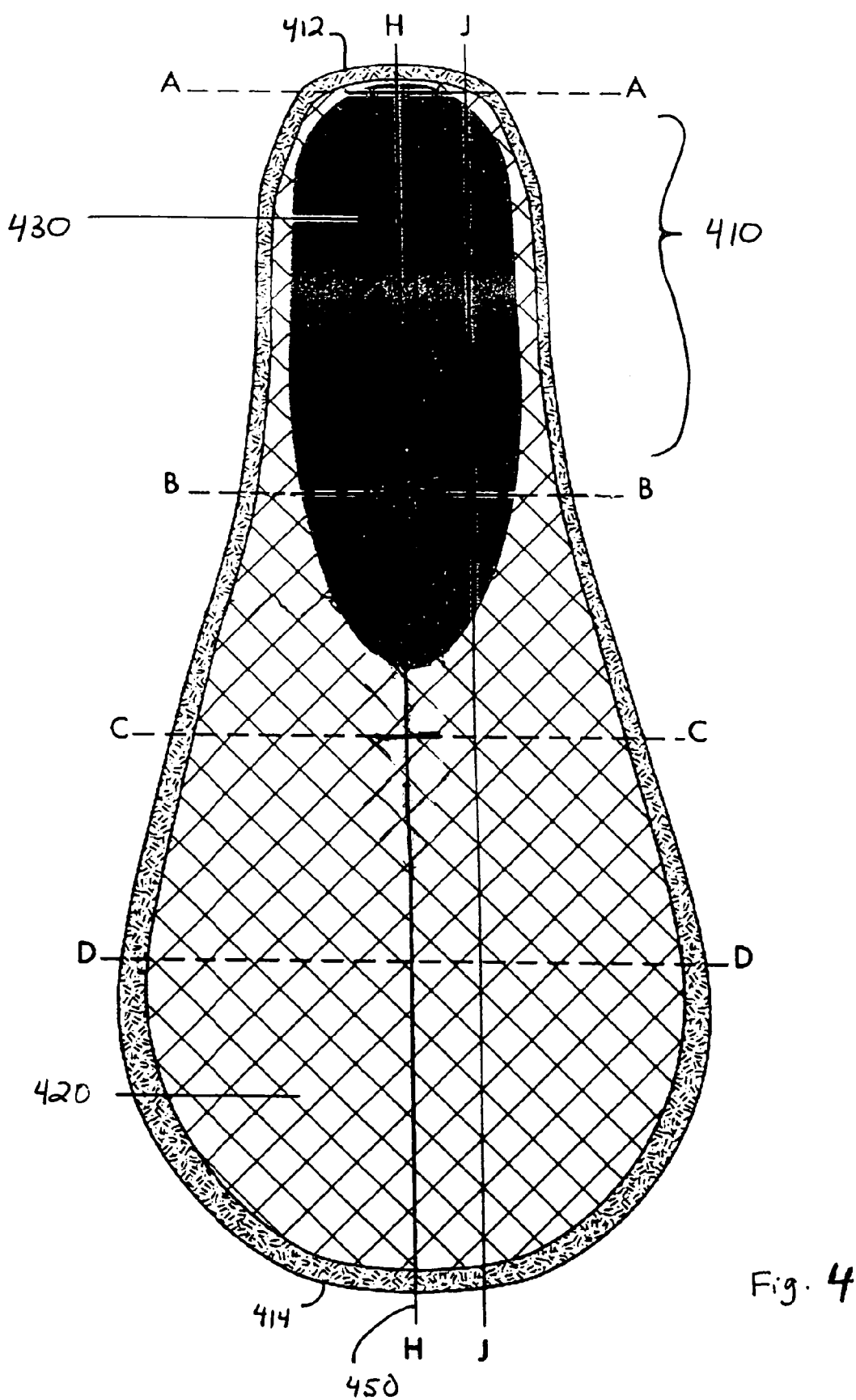
FIG. 4 is a top view of an alternative embodiment of the present invention.

FIG. 4 depicts a top view of an alternative embodiment of the present invention. Also gourd, or pear-shaped, it is narrow at end 410 (portion A-B) that lies in the crotch and abuts the posterior edge of the scrotum in the male. The length of portion A-B 410 is such that narrow end 412 abuts the scrotum when properly applied, but does not ride over it, eliminating scrotal irritation. The liner widens laterally as it emerges posteriorly from the crotch and continues to widen as it extends dorsad over the buttocks to wide end 414, covering the anal area and sufficient area on each buttock. This area is again made sufficiently wide so that normal lateral displacement of underwear, even during athletic activities, does not displace the absorbent item enough to result in leakage. The main portion 420 of the pad, extending over the buttock region, is typically of substantially uniform thickness throughout.

This embodiment provides pad 430 of additional absorbent material that substantially thickens the pantyliner in the narrow region. Thickened area 430 is shaped so that it narrows as it emerges from the crotch to minimize visibility, yet lies within the most ventral portion of the buttock cleft, where fluid drains and where the need for absorbency is the greatest.

Figure 5:
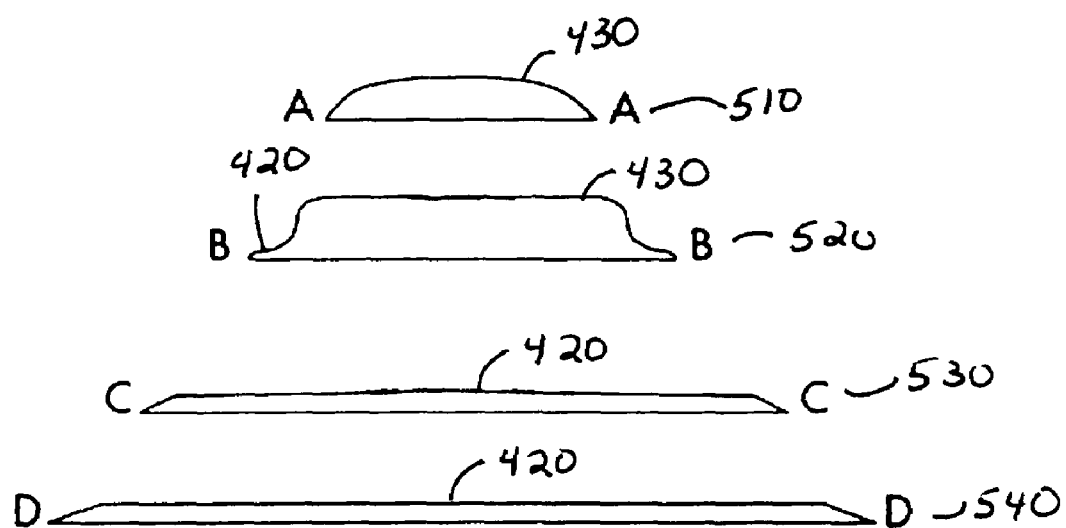
FIG. 5 depicts four transverse sectional views of the embodiment of FIG. 4.

The unique thickness variations in this embodiment of the present invention are depicted in FIG. 5. Transverse sections 510, 520, 530, 540 correspond to lettered cross-sectional lines in FIG. 4. In FIG. 5, section A—A 510 has pad 430 providing a dam of moderate thickness in the lower buttock region. Section B—B 520 has outer edges comprised of main pad 420 and a middle area comprised of moderately thick pad 430. Section C—C 530 and Section D—D 540 are comprised entirely of main pad 420.

Figure 6:
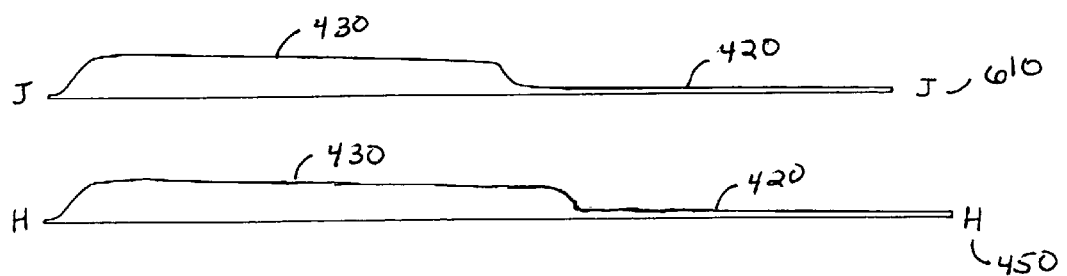
FIG. 6 depicts two longitudinal sectional views of the embodiment of FIG. 4.

FIG. 6 depicts longitudinal sections 610, 620 corresponding to lines H—H and J—J of FIG. 4. In FIG. 6, section J—J 610 is comprised partially of main pad 420 and moderately thick pad 430, as is Section H—H along midline 450.

Figure 7:
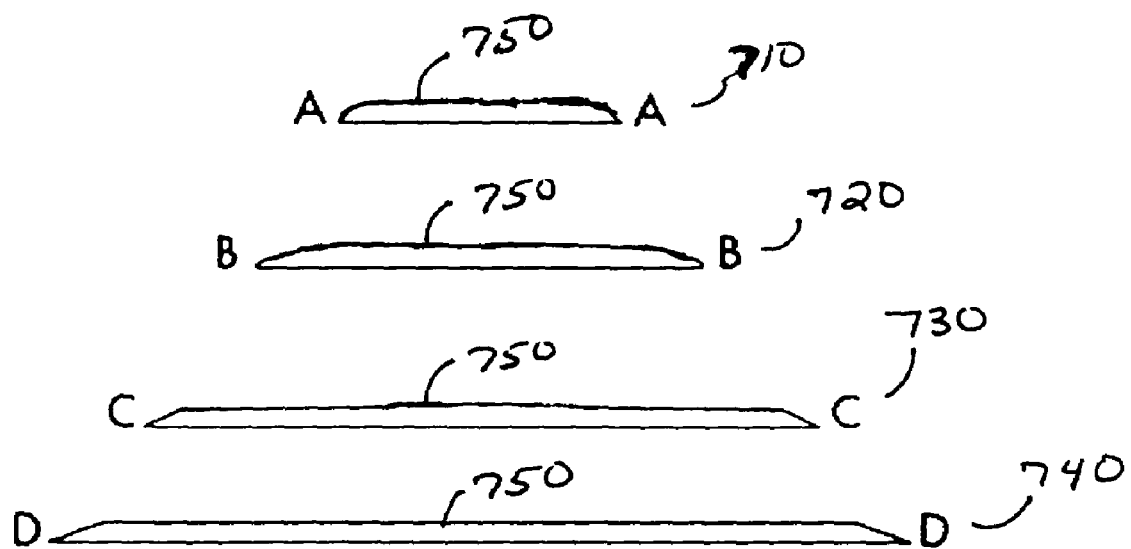
FIG. 7 depicts four transverse sectional views of an alternate embodiment of the present invention.
Figure 8:
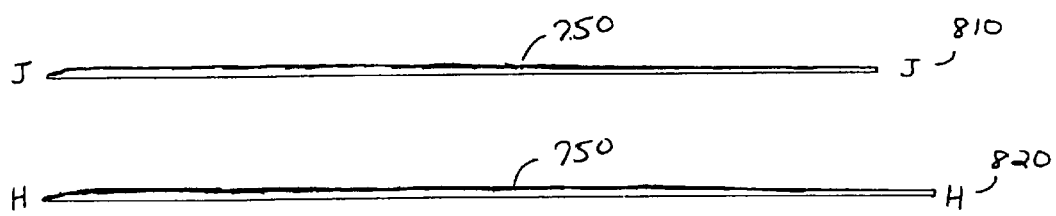
FIG. 8 depicts two longitudinal sectional views of the embodiment of FIG. 7.

The pantyliner made in the unique outline described in this invention can also be of uniform thickness throughout, as shown in the alternative embodiment of FIG. 7. This configuration of the invention is most useful for light discharge. Transverse sections 710, 720, 730, 740 correspond to the lettered cross-sectional lines shown in FIGS. 1 and 4. In FIG. 7, section A—A 710 is comprised solely of main pad 750, as are Section B—B 720, Section C—C 730, and Section D—D 740. FIG. 8 depicts longitudinal sections 810, 820 corresponding to lines H—H and J—J shown in FIGS. 1 and 4. In FIG. 8, section J—J 810 is comprised entirely of main pad 750, as is Section H—H along midline 820.

Figure 9:
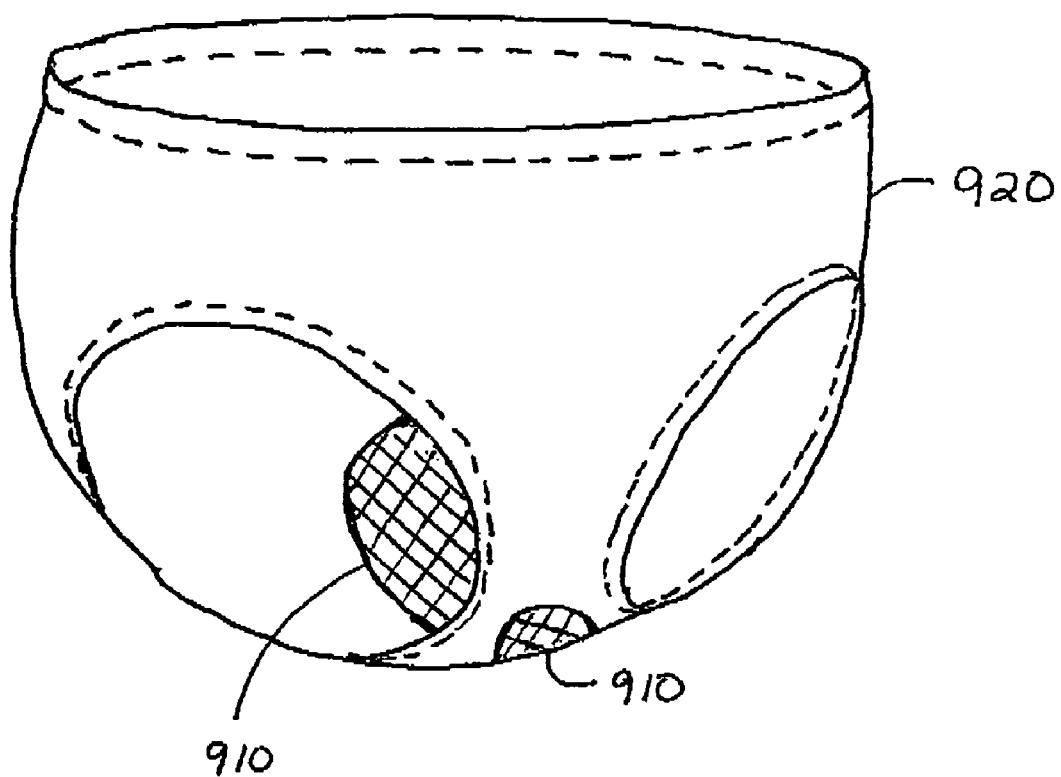
FIG. 9 depicts a front view of an embodiment of the present invention included within a disposable panty.

FIG. 9 depicts a front view of an embodiment of the present invention included within a disposable panty. In FIG. 9, pantyiiner 910 according to the present invention is located within disposable panty 920 in such a position that it will be properly positioned with respect to the buttocks when disposable panty 920 is being worn. Pantyliner 910 may be any of the embodiments of FIGS. 1, 4, or 7. Disposable panty 920 may be, or may be made similarly to, any of the many types of disposable panties known in the art.

A particular advantage of the present invention is that it solves the common psychological problem many men have when needing to buy female absorbent devices. Since this invention specifically addresses the male anatomy and can be marketed as such, it obviates such embarrassment. Moreover, it can be produced in colors that distinguish it from female catamenial devices, thus rendering its use more acceptable to males.

Among the unique features of the present invention are that the device stops at scrotum, rendering it comfortable for use by males. It is a uniquely shaped trilaminar flat sheet, outer impervious, middle absorbent, and inner permeable, for minimal soiling. A preferred embodiment has a unique anti-leak dam, consisting of a thickened area of absorbent material creating a physical dam to absorb moisture. Another preferred embodiment also has a uniquely shaped elongated absorbent structure that lies within the inter-buttock cleft for additional fluid absorbency. Unlike other fecal incontinence products, there are no separate urine/feces compartments, no rigid or semi-rigid shell, and no barriers between "front" and "rear".

It will be obvious to anyone knowledgeable in the art of the invention that the present invention, while incorporating, and adapted to, anatomical constraints particular to the male anatomy may with no, or only minor, adjustment, particularly as to the length of the narrow region, be successfully used for the control of anal leakage in the female as well as the male. The length of portion A-B can be optionally adjusted to cover both the vaginal and urethral orifices in the female. The present invention can be manufactured utilizing a variety of materials, be stretchable or not, and have proportions altered to accommodate different body shapes and sizes. The present invention may also be inserted into, or made as part of, a disposable panty.

The present invention, therefore, provides a unique form of absorbent sanitary device, specifically adapted for the absorption of anal exudates. The anal pantyliner of the present invention absorbs minor leakage or other soiling from the anal area, stays secure during sports and other activities, and is comfortable and secure for males as well as females. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention, which is not to be limited except by the claims that follow.

What is claimed is:

1. An article for protection from anal soiling, the article being adapted for use with a body having a buttocks, a buttocks cleft, and a genital region, comprising:
    an impervious outer layer,
    at least one absorbent middle layer;
    a liquid-permeable body most layer, wherein the article has a wide first end adapted for covering at least part of the buttocks region and a narrow second end adapted for extending just short of the genital region when the first end is positioned over the buttocks region; and
    an additional liquid-absorbent pad of medium thickness extending from the second end to the beginning of the first end and providing a dam adapted to be situated within the ventral portion of the buttock cleft.

2. The article of claim 1, further comprising a midline ridge extending from the center of the second end to the center of the first end and adapted to fit into the buttock cleft.

3. The article of claim 2, further comprising adhesive disposed along the back of the impervious outer layer, for removable attachment of the article to a garment.

4. The article of claim 2, further comprising an attached disposable panty.

5. The article of claim 2, wherein the article has a pear-like shape.

6. The article of claim 2, further comprising an extension on the second end adapted for covering the genital region.

7. The article of claim 1, further comprising adhesive disposed along the back of the impervious outer layer, for removable attachment of the article to a garment.

8. The article of claim 1, further comprising an attached disposable panty.

9. The article of claim 1, wherein the article has a pear-like shape.

10. The article of claim 1, further comprising an extension on the second end adapted for covering the genital region.

11. The article of claim 1, wherein the article is of non-rigid construction.

12. An article for protection from anal soiling, the article being adapted for use with a body having a buttocks, a buttocks cleft, and a genital region, comprising:
    an impervious outer layer;
    at least one absorbent middle layer;
    a liquid-permeable body most layer, wherein the article ha a wide first end adapted from covering at least part of the buttocks region and a narrow second end adapted for extending just short of the genital region when the first end is positioned over the buttocks region; and
    a liquid absorbent midline ridge having a first ridge end located transversely at the center of the second end and a second ridge end ending longitudinally at the center of the first end and adapted to fit into the buttock cleft.

13. The article of claim 12, further comprising adhesive disposed along the back of the impervious outer layer, for removable attachment of the article to a garment.

14. The article of claim 12, further comprising an attached disposable panty.

15. The article of claim 12, wherein the article has a pear-like shape.

16. The article of claim 12, further comprising an extension on the second end adapted for covering the genital region.

17. The article of claim 12, wherein the absorbent middle layer is thickened from the second end to the beginning of the first end, providing a dam adapted to be situated within the ventral portion of the buttock cleft.

* * * * *